United States Patent [19]

Grundler

[11] Patent Number: 5,534,515

[45] Date of Patent: Jul. 9, 1996

[54] PYRROLOPYRIDAZINES HAVING GASTROINTESTINAL PROTECTIVE EFFECTS

[75] Inventor: Gerhard Grundler, Constance, Germany

[73] Assignee: BYK Gulden Lomberg Chemische Fabrik GmbH, Constance, Germany

[21] Appl. No.: 211,990

[22] PCT Filed: Oct. 21, 1992

[86] PCT No.: PCT/EP92/02418

§ 371 Date: Apr. 25, 1994

§ 102(e) Date: Apr. 25, 1994

[87] PCT Pub. No.: WO93/08190

PCT Pub. Date: Apr. 29, 1993

[30] Foreign Application Priority Data

Oct. 25, 1991 [CH] Switzerland ............... 03119/91
Oct. 25, 1991 [CH] Switzerland ............... 03120/91
Oct. 25, 1991 [CH] Switzerland ............... 03123/91

[51] Int. Cl.$^6$ ............... A61K 31/50; C07D 487/04
[52] U.S. Cl. ............... 514/248; 544/236; 548/533
[58] Field of Search ............... 544/236; 514/248

[56] References Cited

U.S. PATENT DOCUMENTS 4,988,695 1/1991 Brown et al. ............... 514/248

FOREIGN PATENT DOCUMENTS 17164 11/1991 WIPO.
06979 4/1992 WIPO.

OTHER PUBLICATIONS

Marquet et al, *Chimie Therapeutique*, 3(5) pp. 348–355 (1968).
Marquet et al, *Chemical Abstracts* vol. 71, No. 38885 (1969).
*Modern Synthetic Reactions* by Herbert O. House, pp. 8–13 (1965).

*Primary Examiner*—Emily Bernhardt
*Attorney, Agent, or Firm*—Jacobson, Price, Holman & Stern

[57] ABSTRACT

Compounds of formula (I)

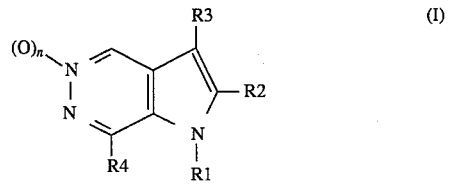

wherein R1 stands for alkyl or R5-substituted alkylene; R2 stands for alkyl; R3 stands for hydrogen, halogen, —CHO (formyl), hydroxymethyl, nitro, amino, or the substituent —CH$_2$O—COR7; R4 stands for halogen or the substituent —A—B—R6; R5 stands for furyl, thienyl, tetrahydrofuryl, phenyl or phenyl substituted by one or two identical or different substituents from the group composed of halogen, alkyl, alkoxy, nitro, —NH—CO—NH$_2$ (ureido), amino, alkylcarbonyl-amino and alkoxycarbonylamino; R7 stands for alkyl, alkoxy-alkyl, alkoxycarbonyl-alkyl or carboxy-alkyl; A stands for O (oxygen) or NH; B stands for a bond, —CH$_2$— (methylene) or —CH$_2$CH$_2$— (1,2-ethylene); and n stands for the number 0 or 1; are useful for preventing and treating gastrointestinal disorders.

13 Claims, 1 Drawing Sheet

PYRROLOPYRIDAZINES HAVING GASTROINTESTINAL PROTECTIVE EFFECTS

This application is a 371 of PCT/EP92/02418, filed Oct. 21, 1992.

FIELD OF APPLICATION OF THE INVENTION

The invention relates to novel compounds, processes for their preparation and their use as active ingredients in medicaments.

KNOWN TECHNICAL BACKGROUND

In J. Heterocyclic Chem. 10, 551 (1973), pyrrolopyridazines substituted in a certain manner are described. In U.S. Pat. No. 4,988,695, pyrrolo- and dihydropyrroloquinolines and their use as gastric acid secretion inhibitors are described.

DESCRIPTION OF THE INVENTION

Figure 1:
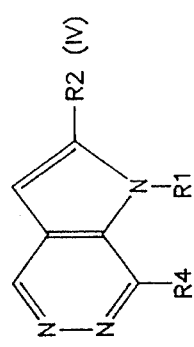
FIGS. 1 to 4 are structural formulae of compounds referred to in the specification by designations I to IV, respectively.

The invention relates to novel compounds of the formula I (see FIG. 1),
wherein
$R1$ is 1–4C-alkyl or $R5$-substituted 1–3C-alkylene,
$R2$ is 1–4C-alkyl,
$R3$ is hydrogen, halogen, CHO (formyl), hydroxymethyl, nitro, amino or the substituent —$CH_2$O—$COR7$,
$R4$ is halogen or the substituent —A—B—$R6$,
$R5$ is furyl, thienyl, tetrahydrofuryl, phenyl or phenyl substituted by one or two identical or different substituents from the group consisting of halogen, 1–4C-alkyl and 1–4C-alkoxy,
$R6$ is hydrogen, thienyl, furyl, phenyl or phenyl substituted by one or two identical or different substituents from the group consisting of halogen, 1–4C-alkyl, 1–4C-alkoxy, nitro, —NH—CO—$NH_2$ (ureido), amino, 1–4C-alkylcarbonylamino and 1–4C-alkoxycarbonylamino,
$R7$ is 1–4C-alkyl, 1–4C-alkoxy-1–4C-alkyl, 1–4C-alkoxycarbonyl-1–4C-alkyl or carboxy-1–4C-alkyl,
A is O (oxygen) or NH,
B is a valence bond, —$CH_2$— (methylene) or —$CH_2CH_2$— (1,2-ethylene) and
n is the number 0 or 1, and the salts of these compounds.

1–4C-alkyl stands for straight-chain or branched alkyl radicals having 1 to 4 carbon atoms. Examples which may be mentioned are the butyl, isobutyl, sec-butyl, tertbutyl, propyl, isopropyl, ethyl and methyl radicals.

1–3C-alkylene stands for trimethylene, ethylene and in particular methylene.

Halogen within the meaning of the present invention is bromine, chlorine or fluorine.

In addition to the oxygen atom, 1–4C-alkoxy radicals contain one of the abovementioned 1–4C-alkyl radicals. The methoxy radical is preferred.

In addition to the carbonyl group, 1–4C-alkylcarbonyl radicals in the 1–4C-alkylcarbonylamino group contain one of the abovementioned 1–4C-alkyl radicals. The acetyl radical is preferred.

In addition to the carbonyl group, 1–4C-alkoxycarbonyl radicals in the 1–4C-alkoxycarbonylamino group contain one of the abovementioned 1–4C-alkoxy radicals. The methoxycarbonyl and the ethoxycarbonyl radicals are preferred.

1–4C-alkoxy-1–4C-alkyl stands for the abovementioned 1–4C-alkyl radicals, to which one of the abovementioned 1–4C-alkoxy radicals is bonded. The methoxymethyl radical is preferred.

1–4C-alkoxycarbonyl-1–4C-alkyl stands for the abovementioned 1–4C-alkyl radicals, to which a 1–4C-alkoxycarbonyl radical (carbonyl with one of the abovementioned 1–4C-alkoxy radicals) is bonded. The methoxycarbonylmethyl and the methoxycarbonylethyl radicals are preferred.

Carboxy-1–4C-alkyl stands for the abovementioned 1–4C-alkyl radicals, to which a carboxyl radical (—COOH) is bonded. The carboxymethyl and the carboxyethyl radicals are preferred.

Suitable salts of compounds of the formula I are preferably all acid addition salts. Particular mention may be made of the pharmacologically tolerable salts of the inorganic and organic acids customarily used in pharmacy. Pharmacologically intolerable salts which, for example, can be obtained initially as process products in the preparation of the compounds according to the invention on the industrial scale, are converted into pharmacologically tolerable salts by processes known to the person skilled in the art. Suitable salts of this type are, for example, water-soluble and water-insoluble acid addition salts, such as the hydrochloride, hydrobromide, hydriodide, phosphate, nitrate, sulfate, acetate, citrate, gluconate, benzoate, hibenzate, fendizoate, butyrate, sulfosalicylate, maleate, laurate, malate, fumarate, succinate, oxalate, tartrate, amsonate, embonate, metembonate, stearate, rosylate, 2-hydroxy-3naphthoate or mesylate.

One embodiment (embodiment a) of the invention is compounds of the formula I in which $R3$ is hydrogen, $R6$ is hydrogen, B is a valence bond and n is the number 0, and $R1$, $R2$, $R4$, $R5$ and A have the meanings indicated at the beginning, and their salts. These compounds are novel intermediates for the preparation of the pharmacologically active final products.

A further embodiment (embodiment b) of the invention is compounds of the formula I in which $R1$, $R2$, $R3$, $R4$, $R5$, $R6$, A, B and n have the meanings indicated at the beginning, with the exception of the meaning hydrogen for $R3$ and $R6$, with the exception of the meaning halogen for $R4$ and with the exception of the meaning valence bond for B, and their salts.

Compounds of embodiment b to be emphasized are those of the formula I, wherein $R1$ is 1–4C-alkyl or $R5$-substituted 1–3C-alkylene,
$R2$ is 1–4C-alkyl,
$R3$ is hydroxymethyl, nitro, amino or the substituent —$CH_2$O—$COR7$,
$R4$ is the substituent —A—B—$R6$,
$R5$ is furyl, thienyl, tetrahydrofuryl, phenyl or phenyl substituted by one or two identical or different substituents from the group consisting of halogen, 1–4C-alkyl and 1–4C-alkoxy,
$R6$ is thienyl, furyl, phenyl or phenyl substituted by one or two identical or different substituents from the group consisting of halogen, 1–4C-alkyl, 1–4C-alkoxy, nitro, —NH—CO—NH₂ (ureido), amino, 1–4C-alkylcarbonylamino and 1–4C-alkoxycarbonylamino, R7 is 1–4C-alkyl, 1–4C-alkoxy-1–4C-alkyl, 1–4C-alkoxycarbonyl-1–4C-alkyl or carboxy-1–4C-alkyl, A is O (oxygen) or NH, B is —CH₂— (methylene) or —CH₂CH₂— (1,2-ethylene) and n is the number 0 or 1, and the salts of these compounds.

Compounds of embodiment b to be particularly emphasized are those of the formula I, wherein R1 is isobutyl or R5-substituted methylene, R2 is 1–4C-alkyl, R3 is hydroxymethyl, nitro, amino or the substituent —CH₂O—COR7, R4 is the substituent —A—B—R6, R5 is furyl, thienyl, phenyl or phenyl substituted by one or two identical or different substituents from the group consisting of halogen, 1–4C-alkyl and 1–4C-alkoxy, R6 is thienyl, phenyl or phenyl substituted by one or two identical or different substituents from the group consisting of halogen, 1–4C-alkyl, 1–4C-alkoxy, —NH—CO—NH₂ (ureido), amino, 1–4C-alkylcarbonylamino and 1–4C - alkoxycarbonylamino, R7 is 1–4C-alkyl, 1–4C-alkoxy-1–4C-alkyl, 1–4C-alkoxycarbonyl-1–4C-alkyl or carboxy-1–4C-alkyl, A is O (oxygen) or NH, B is —CH₂— (methylene) and n is the number 0 or 1, and the salts of these compounds.

Preferred compounds of embodiment b are those of the formula I in which

R1 is R5-substituted methylene,

R2 is 1–4C-alkyl,

R3 is hydroxymethyl, amino or the substituent —CH₂O—COR7,

R4 is the substituent —A—B—R6,

R5 is phenyl or phenyl substituted by a substituent from the group consisting of chlorine, fluorine and b 1–4C-alkoxy, R6 is phenyl or phenyl substituted by a substituent from the group consisting of chlorine and fluorine, R7 is methyl, methoxymethyl, methoxycarbonylmethyl, methoxycarbonylethyl, carboxymethyl or carboxyethyl, A is O (oxygen), B is —CH₂— (methylene) and n is the number 0, and the salts of these compounds.

Particularly preferred compounds of embodiment b are those of the formula I in which R1 is R5-substituted methylene, R2 is 1–4C-alkyl, R3 is hydroxymethyl, amino or the substituent —CH₂O—COR7, R4 is the substituent —A—B—R6, R5 is phenyl or phenyl substituted by methoxy, R6 is phenyl or phenyl substituted by fluorine, R7 is methyl, methoxymethyl or carboxyethyl, A is O (oxygen), B is —CH₂— (methylene) and n is the number 0, and the salts of these compounds.

Compounds according to the invention which may be mentioned by way of example are the compounds of the formula I (see FIG. 1), listed in the following Table 1 with their substituent meanings, and the salts of these compounds (Ph here stands for phenyl, the numbers indicate the positions of the substituents on the phenyl ring):

TABLE 1

Compounds of the formula I (see FIG. 1) in which the substituents have the following meanings

| R1 | R2 | R3 | R4 | R5 | R6 | R7 | n |
|---|---|---|---|---|---|---|---|
| CH₂—R5 | CH₃ | CH₂—OH | OCH₂R6 | Ph | Ph | — | 0 |
| CH₂—R5 | CH₃ | CH₂—OH | OCH₂R6 | Ph | Ph | — | 1 |
| CH₂—R5 | CH₃ | CH₂—OH | OCH₂R6 | Ph | Ph-4-F | — | 0 |
| CH₂—R5 | CH₃ | CH₂—OH | OCH₂R6 | Ph | Ph-4-F | — | 1 |
| CH₂—R5 | CH₃ | CH₂—OH | OCH₂R6 | Ph-4-OCH₃ | Ph | — | 0 |
| CH₂—R5 | CH₃ | CH₂—OH | OCH₂R6 | Ph-4-OCH₃ | Ph-4-F | — | 0 |
| iso-Butyl | CH₃ | CH₂—OH | OCH₂R6 | — | Ph | — | 0 |
| iso-Butyl | CH₃ | CH₂—OH | OCH₂R6 | — | Ph-4-F | — | 0 |
| CH₂—R5 | CH₃ | CH₂—OH | OCH₂R6 | 2-Furyl | Ph | — | 0 |
| CH₂—R5 | CH₃ | CH₂—OH | OCH₂R6 | 2-Furyl | Ph-4-F | — | 0 |
| CH₂—R5 | CH₃ | CH₂—OH | OCH₂R6 | 2-Thienyl | Ph | — | 0 |
| CH₂—R5 | CH₃ | CH₂—OH | OCH₂R6 | 2-Thienyl | Ph-4-F | — | 0 |
| CH₂—R5 | CH₃ | CH₂—OH | OCH₂R6 | 3-Thienyl | Ph | — | 0 |
| CH₂—R5 | CH₃ | CH₂—OH | OCH₂R6 | 3-Thienyl | Ph-4-F | — | 0 |
| CH₂—R5 | CH₃ | CH₂—OH | OCH₂CH₂R6 | Ph | Ph | — | 0 |
| CH₂—R5 | CH₃ | CH₂—OH | OCH₂CH₂R6 | 2-Furyl | Ph | — | 0 |
| CH₂—R5 | CH₃ | CH₂—OH | OCH₂CH₂R6 | Ph-4-OCH₃ | Ph | — | 0 |
| CH₂—R5 | CH₃ | F | NHCH₂R6 | Ph | Ph | — | 0 |
| CH₂—R5 | CH₃ | Cl | OCH₂R6 | Ph | Ph | — | 0 |
| CH₂—R5 | CH₃ | Cl | NHCH₂R6 | Ph | Ph | — | 0 |
| CH₂—R5 | CH₃ | Br | OCH₂R6 | Ph | Ph | — | 0 |
| CH₂—R5 | CH₃ | Br | NHCH₂R6 | Ph | Ph | — | 0 |
| CH₂—R5 | CH₃ | Cl | NHCH₂R6 | 2-Furyl | Ph | — | 0 |
| CH₂—R5 | CH₃ | Br | NHCH₂R6 | 2-Furyl | Ph | — | 0 |
| CH₂—R5 | CH₃ | CHO | OCH₂R6 | Ph | Ph | — | 0 |
| CH₂—R5 | CH₃ | CHO | NHCH₂R6 | Ph | Ph | — | 0 |
| CH₂—R5 | CH₃ | CHO | OCH₂R6 | 2-Furyl | Ph | — | 0 |
| CH₂—R5 | CH₃ | CHO | NHCH₂R6 | 2-Furyl | Ph | — | 0 |
| CH₂—R5 | CH₃ | CH₂OH | OCH₂R6 | Ph | Ph-2-NHCOCH₃ | — | 0 |
| CH₂—R5 | CH₃ | CH₂OH | NHCH₂R6 | Ph | Ph-2-NHCOCH₃ | — | 0 |

TABLE 1-continued

Compounds of the formula I (see FIG. 1) in which the substituents have the following meanings

| R1 | R2 | R3 | R4 | R5 | R6 | R7 | n |
|---|---|---|---|---|---|---|---|
| CH$_2$—R5 | CH$_3$ | Br | NHCH$_2$R6 | Ph | Ph-2-NHCOCH$_3$ | — | 0 |
| CH$_2$—R5 | CH$_3$ | Cl | NHCH$_2$R6 | Ph | Ph-2-NHCOCH$_3$ | — | 0 |
| CH$_2$—R5 | CH$_3$ | CH$_2$OH | OCH$_2$R6 | Ph | Ph-2-NHCOCH$_3$-6-CH$_3$ | — | 0 |
| CH$_2$—R5 | CH$_3$ | CH$_2$OH | NHCH$_2$R6 | Ph | Ph-2-NHCOCH$_3$-6-CH$_3$ | — | 0 |
| CH$_2$—R5 | CH$_3$ | Br | NHCH$_2$R6 | Ph | Ph-2-NHCOCH$_3$-6-CH$_3$ | — | 0 |
| CH$_2$—R5 | CH$_3$ | Cl | NHCH$_2$R6 | Ph | Ph-2-NHCOCH$_3$-6-CH$_3$ | — | 0 |
| CH$_2$—R5 | CH$_3$ | CH$_2$OH | OCH$_2$R6 | Ph | Ph-2-NHCOOCH$_3$-6-CH$_3$ | — | 0 |
| CH$_2$—R5 | CH$_3$ | CH$_2$—OH | NHCH$_2$R6 | Ph | Ph | — | 0 |
| CH$_2$—R5 | CH$_3$ | CH$_2$—OH | NHCH$_2$R6 | Ph-4-OCH$_3$ | Ph | — | 0 |
| CH$_2$—R5 | CH$_3$ | CH$_2$—OH | NHCH$_2$R6 | 2-Furyl | Ph | — | 0 |
| CH$_2$—R5 | CH$_3$ | F | OCH$_2$R6 | Ph | Ph | — | 0 |
| CH$_2$—R5 | CH$_3$ | CH$_2$OH | NHCH$_2$R6 | Ph | Ph-2-NHCOOCH$_3$-6-CH$_3$ | — | 0 |
| CH$_2$—R5 | CH$_3$ | Br | NHCH$_2$R6 | Ph | Ph-2-NHCOOCH$_3$-6-CH$_3$ | — | 0 |
| CH$_2$—R5 | CH$_3$ | Cl | NHCH$_2$R6 | Ph | Ph-2-NHCOOCH$_3$-6-CH$_3$ | — | 0 |
| CH$_2$—R5 | CH$_3$ | CH$_2$OH | OCH$_2$R6 | Ph | 2-Thienyl | — | 0 |
| CH$_2$—R5 | CH$_3$ | CH$_2$OH | OCH$_2$R6 | Ph | 3-Thienyl | — | 0 |
| CH$_2$—R5 | CH$_3$ | CH$_2$OH | NHCH$_2$R6 | Ph | 2-Thienyl | — | 0 |
| CH$_2$—R5 | CH$_3$ | CH$_2$OH | NHCH$_2$R6 | Ph | 3-Thienyl | — | 0 |
| CH$_2$—R5 | CH$_3$ | NH$_2$ | OCH$_2$R6 | Ph | Ph | — | 0 |
| CH$_2$—R5 | CH$_3$ | NH$_2$ | NHCH$_2$R6 | Ph | Ph | — | 0 |
| CH$_2$—R5 | CH$_3$ | NH$_2$ | OCH$_2$R6 | Ph | Ph-4-F | — | 0 |
| CH$_2$—R5 | CH$_3$ | NH$_2$ | NHCH$_2$R6 | Ph | Ph-4-F | — | 0 |
| iso-Butyl | CH$_3$ | NH$_2$ | OCH$_2$R6 | — | Ph | — | 0 |
| iso-Butyl | CH$_3$ | NH$_2$ | OCH$_2$R6 | — | Ph-4-F | — | 0 |
| iso-Butyl | CH$_3$ | NH$_2$ | NHCH$_2$R6 | — | Ph | — | 0 |
| iso-Butyl | CH$_3$ | NH$_2$ | NHCH$_2$R6 | — | Ph-4-F | — | 0 |
| iso-Butyl | CH$_3$ | NO$_2$ | OCH$_2$R6 | — | Ph | — | 0 |
| iso-Butyl | CH$_3$ | NO$_2$ | OCH$_2$R6 | — | Ph-4-F | — | 0 |
| iso-Butyl | CH$_3$ | NO$_2$ | NHCH$_2$R6 | — | Ph | — | 0 |
| iso-Butyl | CH$_3$ | NO$_2$ | NHCH$_2$R6 | — | Ph-4-F | — | 0 |
| CH$_2$—R5 | CH$_3$ | CH$_2$O—COR7 | OCH$_2$R6 | Ph | Ph | CH$_3$ | 0 |
| CH$_2$—R5 | CH$_3$ | CH$_2$O—COR7 | OCH$_2$R6 | Ph | Ph-4-F | CH$_3$ | 0 |
| CH$_2$—R5 | CH$_3$ | CH$_2$O—COR7 | OCH$_2$R6 | 2-Furyl | Ph | CH$_3$ | 0 |
| CH$_2$—R5 | CH$_3$ | CH$_2$O—COR7 | OCH$_2$R6 | 2-Furyl | Ph-4-F | CH$_3$ | 0 |
| iso-Butyl | CH$_3$ | CH$_2$O—COR7 | OCH$_2$R6 | — | Ph | CH$_3$ | 0 |
| iso-Butyl | CH$_3$ | CH$_2$O—COR7 | OCH$_2$R6 | — | Ph-4-F | CH$_3$ | 0 |
| CH$_2$—R5 | CH$_3$ | CH$_2$O—COR7 | OCH$_2$R6 | Ph-4-OCH$_3$ | Ph | CH$_3$ | 0 |
| CH$_2$—R5 | CH$_3$ | CH$_2$O—COR7 | OCH$_2$R6 | Ph-4-OCH$_3$ | Ph-4-F | CH$_3$ | 0 |
| CH$_2$—R5 | CH$_3$ | CH$_2$O—COR7 | OCH$_2$R6 | Ph | Ph | CH$_2$OCH$_3$ | 0 |
| CH$_2$—R5 | CH$_3$ | CH$_2$O—COR7 | OCH$_2$R6 | Ph | Ph-4-F | CH$_2$OCH$_3$ | 0 |
| CH$_2$—R5 | CH$_3$ | CH$_2$O—COR7 | OCH$_2$R6 | 2-Furyl | Ph | CH$_2$OCH$_3$ | 0 |
| CH$_2$—R5 | CH$_3$ | CH$_2$O—COR7 | OCH$_2$R6 | 2-Furyl | Ph-4-F | CH$_2$OCH$_3$ | 0 |
| CH$_2$—R5 | CH$_3$ | CH$_2$O—COR7 | OCH$_2$R6 | Ph-4-OCH$_3$ | Ph | CH$_2$OCH$_3$ | 0 |
| CH$_2$—R5 | CH$_3$ | CH$_2$O—COR7 | OCH$_2$R6 | Ph-4-OCH$_3$ | Ph-4-F | CH$_2$OCH$_3$ | 0 |
| iso-Butyl | CH$_3$ | CH$_2$O—COR7 | OCH$_2$R6 | — | Ph | CH$_2$OCH$_3$ | 0 |
| iso-Butyl | CH$_3$ | CH$_2$O—COR7 | OCH$_2$R6 | — | Ph-4-F | CH$_2$OCH$_3$ | 0 |
| CH$_2$—R5 | CH$_3$ | CH$_2$O—COR7 | OCH$_2$R6 | Ph | Ph | CH$_2$CH$_2$COOH | 0 |
| CH$_2$—R5 | CH$_3$ | CH$_2$O—COR7 | OCH$_2$R6 | Ph | Ph-4-F | CH$_2$CH$_2$COOH | 0 |
| CH$_2$—R5 | CH$_3$ | CH$_2$O—COR7 | OCH$_2$R6 | 2-Furyl | Ph | CH$_2$CH$_2$COOH | 0 |
| CH$_2$—R5 | CH$_3$ | CH$_2$O—COR7 | OCH$_2$R6 | 2-Furyl | Ph-4-F | CH$_2$CH$_2$COOH | 0 |
| CH$_2$—R5 | CH$_3$ | CH$_2$O—COR7 | OCH$_2$R6 | Ph-4-OCH$_3$ | Ph | CH$_2$CH$_2$COOH | 0 |
| CH$_2$—R5 | CH$_3$ | CH$_2$O—COR7 | OCH$_2$R6 | Ph-4-OCH$_3$ | Ph-4-F | CH$_2$CH$_2$COOH | 0 |
| CH$_2$—R5 | CH$_3$ | CH$_2$O—COR7 | OCH$_2$R6 | Ph | Ph | CH$_2$CH$_2$COOCH$_3$ | 0 |
| CH$_2$—R5 | CH$_3$ | CH$_2$O—COR7 | OCH$_2$R6 | Ph | Ph-4-F | CH$_2$CH$_2$COOCH$_3$ | 0 |
| CH$_2$—R5 | CH$_3$ | CH$_2$O—COR7 | OCH$_2$R6 | 2-Furyl | Ph | CH$_2$CH$_2$COOCH$_3$ | 0 |
| CH$_2$—R5 | CH$_3$ | CH$_2$O—COR7 | OCH$_2$R6 | 2-Furyl | Ph-4-F | CH$_2$CH$_2$COOCH$_3$ | 0 |
| CH$_2$—R5 | CH$_3$ | CH$_2$O—COR7 | OCH$_2$R6 | Ph-4-OCH$_3$ | Ph | CH$_2$CH$_2$COOCH$_3$ | 0 |
| CH$_2$—R5 | CH$_3$ | CH$_2$O—COR7 | OCH$_2$R6 | Ph-4-OCH$_3$ | Ph-4-F | CH$_2$CH$_2$COOCH$_3$ | 0 |
| CH$_2$—R5 | CH$_3$ | CH$_2$O—COR7 | OCH$_2$R6 | Ph | Ph | CH$_2$COOH | 0 |
| CH$_2$—R5 | CH$_3$ | CH$_2$O—COR7 | OCH$_2$R6 | Ph | Ph-4-F | CH$_2$COOH | 0 |
| CH$_2$—R5 | CH$_3$ | CH$_2$O—COR7 | OCH$_2$R6 | 2-Furyl | Ph | CH$_2$COOH | 0 |
| CH$_2$—R5 | CH$_3$ | CH$_2$O—COR7 | OCH$_2$R6 | 2-Furyl | Ph-4-F | CH$_2$COOH | 0 |

Figure 2:
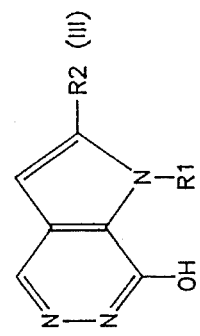
Figure 3:
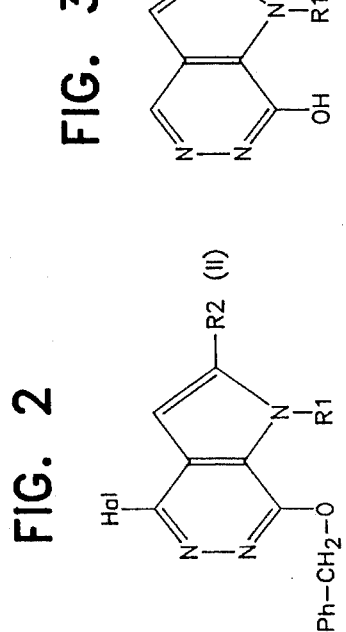
Figure 4:
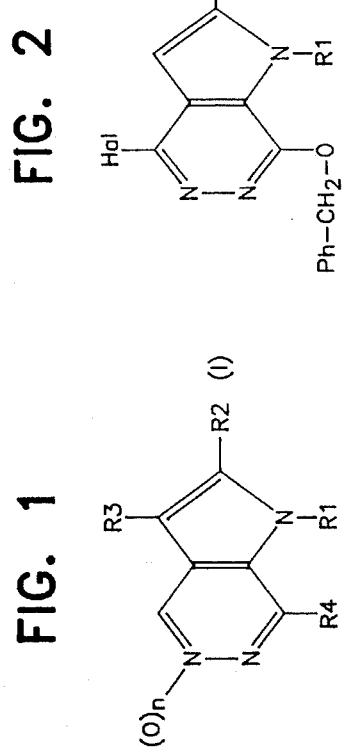

The invention further relates to a process for the preparation of the compounds according to the invention and their salts. The process comprises a) for the preparation of compounds I in which R3 and R6 denote hydrogen, R4 denotes the substituent —A—B—R6, A denotes oxygen, B denotes a valence bond and n denotes the number 0, reductively debenzylating and dehalogenating compounds of the formula II (see FIG. 2), in which R1 and R2 have the meanings indicated above and Hal is a halogen atom, preferably a chlorine atom, or b) for the preparation of compounds I in which R3 denotes hydrogen, R4 denotes halogen and n denotes the number 0, reacting the compounds of the formula III (see FIG. 3), in which R1 and R2 have the meanings indicated above, obtained as in a) with suitable halogenating agents, or c) for the preparation of compounds I in which R3 denotes hydrogen, R4 denotes the substituent —A—B—R6 and n denotes the number 0, reacting the compounds of the formula IV (see FIG. 4), in which R4 denotes halogen, obtained as in b) with compounds of the formula H—A—B—R6 (=compounds of the formula V), in which A, B and R6 have the meanings indicated above, or their salts with bases, or d) for the preparation of compounds I in which R3 denotes halogen and n denotes the number 0, reacting compounds of the formula IV, in which R1, R2 and R4 have the meanings indicated above, with suitable halogenating agents, or e) for the preparation of compounds I in which R3 denotes CHO (formyl) and n denotes the number 0, intermediately metalating compounds of the formula I, in which R3 denotes halogen, in the 3-position and subsequently reacting with dimethylformamide or formic acid esters, or f) for the preparation of compounds I in which R3 denotes hydroxymethyl and n denotes the number 0, reducing compounds of the formula I in which R3 denotes CHO (formyl), or g) for the preparation of compounds I in which n denotes the number 1, oxidizing compounds of the formula I in which n denotes the number 0, or h) for the preparation of compounds I in which R4 denotes the radical —A—B—R6, where R6 denotes phenyl substituted by 1–4C-alkoxycarbonylamino or 1–4C-alkylcarbonylamino, reacting compounds of the formula I, in which R4 denotes the radical —A—B—R6, where R6 denotes phenyl substituted by amino, with 1–4C-alkyl haloformates or with 1–4C-carboxylic acid halide, or i) for the preparation of compounds I in which R3 denotes nitro and R4 denotes halogen, nitrating compounds of the formula I in which R3 denotes hydrogen and R4 denotes halogen, or j) for the preparation of compounds I in which R3 denotes nitro and R4 denotes the substituent —A—B—R6, reacting the compounds of the formula I, in which R3 denotes nitro and R4 denotes halogen, obtained as in i) with compounds of the formula H—A—B—R6 (=compounds of the formula V), in which A, B and R6 have the meanings indicated above, or their salts with bases, or k) for the preparation of compounds I in which R3 denotes amino and R4 denotes the substituent —A—B—R6, reducing the compounds of the formula I, in which R3 denotes nitro and R4 denotes the substituent —A—B—R6, obtained as in j), or l) for the preparation of compounds I in which R3 denotes the substituent —CH$_2$O—COR7 and R7 denotes 1–4C-alkyl, 1–4C-alkoxy-1–4C-alkyl, 1–4C-alkoxycarbonyl-1–4C-alkyl or carboxy-1–4C-alkyl, reacting compounds of the formula I in which R3 denotes hydroxymethyl with compounds of the formula R7—CO—Z (=compounds of the formula VI) in which R7 has the above meanings and Z is OH (hydroxyl) or a suitable leaving group, and, if desired, subsequently converting the compounds I obtained according to a), b), c), d), e), f), g), h), i), j), k) or l) into their salts, or, if desired, subsequently liberating the compounds I from salts of the compounds I obtained.

The reductive debenzylation and dehalogenation as in process variant a) is carried out in a manner familiar to the person skilled in the art, e.g. using hydrogen in the presence of palladium as a catalyst, in methanol at room temperature.

The halogenation of the compounds of the formula III is carried out in the presence of suitable solvents or preferably without solvents. Possible suitable solvents are only anhydrous solvents, such as e.g. open-chain or cyclic ethers (diethyl ether, diethylene glycol dimethyl ether, dioxane or tetrahydrofuran), or (aromatic) hydrocarbons, such as e.g. cyclohexane, benzene or toluene, which are inert to the halogenating agent.

Possible halogenating agents are all known halogen-eliminating reagents, in particular those compounds which are suitable for use on the industrial scale. Examples which may be mentioned are phosphorus trichloride, phosphorus tribromide, thionyl chloride, thionyl bromide, phosphorus oxychloride or phosphorus oxybromide.

The halogenation is carried out (depending on the nature of the halogenating agent and of the solvent optionally employed) at temperatures between 0° and 150° C., in particular at the boiling point of the solvent or halogenating agent used.

The reaction of the compounds IV with the compounds of the formula V as in process variant c) is carried out (depending on the nature of the compound V) in an anhydrous, inert solvent or without further solvent addition using an excess of compound V as solvent. Possible anhydrous, inert solvents are in particular aprotic, polar solvents, such as e.g. dimethyl sulfoxide, tetrahydrofuran, dioxane or dimethylformamide.

Depending on the nature of the compounds V, their reaction with the compounds IV necessitates the presence of an auxiliary base or (if A has the meaning NH in compound V) an excess of compound V. Possible auxiliary bases are, for example, organic amines (such as triethylamine or diisopropylamine), alkali metal carbonates (such as sodiumcarbonate or potassium carbonate) or alkali metal hydroxides (such as sodium hydroxide or potassium hydroxide), but preferably those compounds which are able to deprotonate the compounds V smoothly. Mention may be made here in particular of metal hydrides (e.g. sodium hydride) or alkali metals (e.g. sodium), which are either employed for the deprotonation of the compound V before the reaction with IV or are added to the reaction mixture of IV and V. In a preferred process variant, the deprotonation can also be carried out by an alkali metal alkoxide, such as, for example, potassium tert-butoxide, in the presence of a crown ether, such as, for example, [18]crown-6.

The reaction temperature—depending on the reactivity of the compound V or its salts with bases—is between 0° and 150° C., temperatures between 0° and 50° sufficing if the reactivity is higher, but higher temperatures being necessary if the reactivity is lower, the boiling point of the solvent used or of the excess of compound V used as solvent being preferred.

The halogenation as in process variant d) is carried out in a manner familiar to the person skilled in the art, for example by direct reaction with the halogen in suitable solvents, for example in dichloromethane, at temperatures of preferably around or below 0° C., or by reaction with suitable halogenating agents, such as, for example, n-bromo- or n-chloro-succinimide, in inert solvents, such as, for example, dichloromethane or dimethylformamide.

The intermediate metalation as in process variant e) can be carried out, for example, in the form of a Grignard reaction or using butyllithium as a reagent. The metalation is carried out under reaction conditions and in solvents that are familiar to the person skilled in the art for carrying out reactions with organometallic compounds. The following reaction with dimethylformamide or formic acid esters is likewise carried out in a manner known per se.

The reduction of the formyl group to the hydroxymethyl group as in process variant f) is likewise carried out in a manner familiar to the person skilled in the art, for example by reaction with sodium borohydride in a suitable solvent, such as e.g. ethanol.

The N-oxidation as in process variant g) is carried out in a manner known per se using customary oxidants, the N-oxidation preferably being carried out using m-chloroperoxybenzoic acid in dichloromethane at room temperature.

The conversion of the amino group to the alkoxycarbonylamino or alkylcarbonylamino group as in process variant h) is carried out in a manner known per se for urethane or amide preparation, preferably by reaction of the amino compounds with appropriate chloroformic acid esters or with appropriate carbonyl chlorides.

The nitration as in process variant i) is carried out in a manner familiar to the person skilled in the art using nitrating acid (nitric acid/sulfuric acid) under the customary reaction conditions.

The reaction as in process variant j) is carried out in an analogous manner to that described for process variant c).

The reduction as in process variant k) is carried out under conditions which are as gentle as possible, for example using sodium dithionite as a reductant and under reaction conditions as are customary in the use of this reductant.

The reaction of the compounds I where R3=hydroxymethyl with the compounds VI as in process variant 1) is carried out in a manner known per se, as is known to the person skilled in the art on the basis of his expert knowledge about esterification reactions. The esterification is carried out in inert solvents, such as, for example, dioxane or tetrahydrofuran, and, depending on the nature of the group Z, either in the presence of an agent which eliminates water or chemically binds it, such as, for example, dicyclohexylcarbodiimide (if Z=OH), or in the presence of an auxiliary base (e.g. triethylamine) if Z is a leaving group, for example a halogen atom (in particular chlorine). If R7 is a carboxy-1–4C-alkyl radical, an alkoxycarbonyloxy radical (mixed anhydride), in particular the isobutoxycarbonyloxy radical, is preferably employed as the leaving group Z without further addition of a water-eliminating agent.

The isolation and purification of the substances according to the invention obtained as in process variants a) to 1) is carried out in a manner known per se e.g. in such a way that the solvent is distilled off in vacuo and the residue obtained is recrystallized from a suitable solvent or subjected to one of the customary purification methods, such as, for example, column chromatography on suitable support material.

Acid addition salts are obtained by dissolving the free compounds in a suitable solvent, e.g. in a chlorinated hydrocarbon, such as methylene chloride or chloroform, or a low molecular weight aliphatic alcohol (ethanol, isopropanol) which contains the desired acid, or to which the desired acid is subsequently added.

The salts are obtained by filtering, reprecipitating, precipitating with a nonsolvent for the addition salt or by evaporating the solvent. By rendering alkaline, e.g. with aqueous ammonia solution, salts obtained can be converted to the free compounds, which in turn can be converted to acid addition salts. In this manner, pharmacologically nontolerable acid addition salts can be converted to pharmacologically tolerable acid addition salts.

Figure 5:
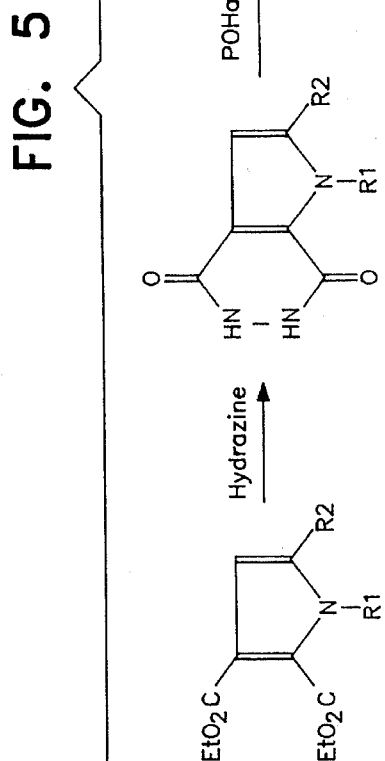
FIG. 5 is a synthesis scheme for preparing compounds of formula II.

The compounds of the formula II can be prepared according to the general synthesis scheme indicated in FIG. 5, for example in such a way as is shown as an example in the following examples.

The pyrroles shown as starting compounds in the synthesis scheme are known [see e.g. R. G. Jones, J. Am. Chem. Soc. 77, 4069 (1955); ibid. 78, 159 (1956)] or they can be prepared from known compounds in a manner known per se.

The following examples illustrate the invention in greater detail without restricting it. The compounds of the general formula I and the salts of these compounds listed by name in the examples are a preferred subject of the invention. m.p.: denotes melting point, the abbreviation h is used for hours and the abbreviation min for minutes. "Ether" is understood as meaning diethyl ether.

EXAMPLES

Final products and intermediates 1a. 1-Benzyl-7-(4-fluorobenzyloxy)-3-hydroxymethyl-2-methylpyrrolo[2,3-d]pyridazine A solution of 780 mg (2.08 mmol) of 1-benzyl-7-(4-fluorobenzyloxy) 3-formyl-2 -methylpyrrolo [2,3-d]pyridazine in 50 ml of ethanol is treated with 80 mg (2.1 mmol) of sodium borohydride and stirred at room temperature for 30 min. After addition of 100 ml of water, the mixture is concentrated on a rotary evaporator to half the volume. The precipitate is filtered off, washed with 50 ml of water and dried in a high vacuum over potassium hydroxide. 670 mg (85%) of the title compound are isolated. M.p.: 122°–124° C.

1b. 1-Benzyl-7-benzyloxy-3-hydroxymethyl-2-methylpyrrolo[2,3-d]pyridazine 1.3 g (3.6 mmol) of 1-benzyl-7-benzyloxy-3-formyl-2-methylpyrrolo[2,3-d]pyridazine and 140 mg (3.7 mmol) of sodium borohydride are reacted in 125 ml of ethanol as described for Example 1a. Yield: 92%, m.p.: 130°–132° C.

1c. 1-Benzyl-7-benzylamino-3-hydroxymethyl-2-methylpyrrolo[2,3-d]pyridazine 0.2 g (0.56 mmol) of 1-benzyl-7-benzylamino-3-formyl-2-methylpyrrolo[2,3-d]pyridazine and 23 mg (0.62 mmol) of sodium borohydride are reacted in 20 ml of methanol as described for Example 1a. Yield: 80%, m.p.: 238°–240° C.

2a. 1-Benzyl-7-(4-fluorobenzyloxy)-3-formyl-2-methylpyrrolo[2,3-d]pyridazine

A solution of 810 mg (1.9 mmol) of 1-benzyl-3-bromo-7-(4-fluorobenzyloxy)-2-methylpyrrolo[2,3-d]pyridazine in 30 ml of anhydrous tetrahydrofuran is cooled to −70° C. under argon and treated with 1.65 ml (2.7 mmol) of a 15% strength solution of n-butyllithium in hexane. The mixture is subsequently stirred at −70° C. for a further 30 min. After addition of 215 µl (2.7 mmol) of anhydrous dimethylformamide, the temperature is kept at −70° C. for a further 30 min and subsequently slowly increased to 20° C. The solution is then treated with 100 ml of water and extracted with 3×50 ml of ethyl acetate. The organic extracts are washed with 50 ml of water, dried over magnesium sulfate and concentrated. The residue which remains is chromatographed on silica gel (eluent: ethyl acetate). After concentration of the fractions of Rf=0.4 and crystallization from diisopropyl ether, 150 mg (21%) of the title compound are isolated. M.p.: 136°–141° C.

2b. 7-Benzyloxy-3-formyl-1-(4-methoxybenzyl)-2-methylpyrrolo[2,3-d]pyridazine 440 mg (1.0 mmol) of 7-benzyloxy-3-bromo-1-(4-methoxybenzyl)-2-methylpyrrolo[2,3-d]pyridazine, 735 μl (1.2 mmol) of a 15% strength solution of n-butyllithium in hexane and 160 μl (1.2 mmol) of dimethylformamide are reacted in 25 ml of tetrahydrofuran as described for Example 2a. Yield: 36%, m.p.: 139°–145° C.

2c. 1-Benzyl-7-benzyloxy-3-formyl-2-methylpyrrolo-[2,3-d]pyridazine 5.0g (12.2 mmol) of 1-benzyl-7-benzyloxy-3-bromo-2-methylpyrrolo[2,3-d]pyridazine, 9 ml (14.7 mmol) of a 15% strength solution of n-butyllithium in hexane and 2.4 ml (29.4 mmol) of dimethylformamide are reacted in 125 ml of anhydrous tetrahydrofuran as described for Example 2a. Yield: 32%, m.p.: 147°–149° C.

2d. 1-Benzyl-7-benzylamino-3-formyl-2-methylpyrrolo-[2,3-d]pyridazine 0.58 g (1.4 mmol) of 1-benzyl-7-benzylamino-3-bromo-2-methylpyrrolo[2,3-d]pyridazine, 3.5 ml (5.7 mmol) of 15% strength solution of n-butyllithium in hexane and 0.55 ml (7 mmol) of dimethylformamide are reacted in 40 ml of anhydrous tetrahydrofuran as described for Example 2a. Yield: 44%, m.p.: 171°–172° C.

3a. 1-Benzyl-3-bromo-7-(4-fluorobenzyloxy)-2-methylpyrrolo[2,3-d]pyridazine

A solution of 180 μl (3.5 mmol) of bromine in 7 ml of anhydrous dichloromethane is added dropwise at 0° C. to a solution of 910 mg (2.6 mmol) of 1-benzyl-7-(4-fluorobenzyloxy)-2-methylpyrrolo[2,3-d]pyridazine in 15 ml of anhydrous dichloromethane in the course of 30 min. The solution is kept at 0° C. for a further 1 h, then treated with 50 ml of ice-water and extracted. The organic phase is separated off, washed with 3×25 ml of water, dried over magnesium sulfate and concentrated. The residue is chromatographed on silica gel (eluent: ethyl acetate). The fractions of Rf=0.6 are concentrated and crystallized from diisopropyl ether/cyclohexane. 880 mg (79%) of the title compound are isolated. M.p.: 128°–130° C.

3b. 7-Benzyloxy-3-bromo-1-(4-methoxybenzyl)-2-methylpyrrolo[2,3-d]pyridazine 1.8 g (5 mmol) of 7-benzyloxy-1-(4-methoxybenzyl)-2-methylpyrrolo[2,3-d]pyridazine and 282 μl (5.5 mmol) of bromine are reacted in a total of 65 ml of dichloromethane and purified as described for Example 3a. Yield: 78%, m.p.: 149°–152° C.

3c. 1-Benzyl-7-benzyloxy-3-bromo-2-methylpyrrolo[2,3-d]pyridazine 42.3 g (0.128 mol) of 1-benzyl-7-benzyloxy-2-methylpyrrolo[2,3-d]pyridazine and 6.6 ml (0.128 mol) of bromine are reacted in a total of 200 ml of dichloromethane as described for Example 3a. Yield: 85%, m.p.: 122°–123° C.

3d. 1-Benzyl-3-bromo-7-chloro-2-methylpyrrolo[2,3-d]pyridazine 8.0 g (31 mmol) of 1-benzyl-7-chloro-2-methylpyrrolo[2,3-d]pyridazine and 1.59 ml (31 mmol) of bromine are reacted in a total of 150 ml of dichloromethane as described for Example 3a. Yield: 83%, m.p.: 138°–140° C.

4a. 1-Benzyl-7-(4-fluorobenzyloxy)-2-methylpyrrolo[2,3-d]pyridazine 32.65 g (291 mmol) of potassium tert-butoxide and 1.54 g (5.82 mmol) of [18]crown-6 (98% strength) are added successively to a solution of 21.8 g (173 mmol) of 4-fluorobenzyl alcohol in 150 ml of anhydrous N-methylpyrrolidone. This mixture is stirred at room temperature for 1 h. A solution of 15.0 g (58.2 mmol) of 1-benzyl-7-chloro-2-methylpyrrolo[2,3-d]pyridazine in 100 ml of anhydrous N-methylpyrrolidone is subsequently added dropwise in the course of 30 min. The mixture is stirred at room temperature for a further 15 min, then treated with 500 ml of ice-water and extracted with 3×400 ml of ethyl acetate. The organic extracts are washed with 3×300 ml of water and subsequently dried over magnesium sulfate. After concentration and crystallization from diisopropyl ether, 12.95 g (64%) of the title compound are isolated. M.p.: 127°–132° C.

The following are prepared in an analogous manner:

4b. 7-Benzyloxy-1-(4-methoxybenzyl)-2-methylpyrrolo[2,3-d]pyridazine 5.63 g (52 mmol) of benzyl alcohol, 90 ml of N-methylpyrrolidone, 9.75 g (87mmol) of potassium tert-butoxide, 0.46 g (1.74 mmol) of [18]crown-6 and 5.0 g (17 mmol) of 7-chloro-1-(4-methoxybenzyl)-2-methylpyrrolo[2,3-d]pyridazine are reacted at room temperature for 2 h. Purification: crystallization from ethyl acetate, concentration of the mother liquor and chromatography on silica gel (eluent: toluene/dioxane = 9:1). Yield: 80%, m.p.: 152°–156° C.

4c. 1-Benzyl-7-benzyloxy-2-methylpyrrolo[2,3-d]pyridazine 650 mg (6 mmol) of benzyl alcohol, 10 ml of N-methylpyrrolidone, 1.1 g (10 mmol) of potassium tert-butoxide, 50 mg (0.2 retool) of [18]crown-6 and 500 mg (1.94 retool) of 1-benzyl-7-chloro-2-methylpyrrolo[2,3-d]pyridazine are reacted at room temperature for 2 h. Purification: chromatography on silica gel (eluent: toluene/dioxane=2:1) and crystallization from diisopropyl ether. Yield: 68%, m.p.: 124° C.

5a. 3-Amino-7-benzyloxy-1-isobutyl-2-methylpyrrolo[2,3-d]pyridazine fumarate A suspension of 1.0 g (2.94 mmol) of 7-benzyloxy-1-isobutyl-2-methyl-3-nitropyrrolo [2,3-d]pyridazine in 30 ml of methanol is treated with a solution of 2.6 g (14.6 mmol) of sodium dithionite in 30 ml of water and stirred at 70° C. for 30 min. After addition of 100 ml of water, the mixture is extracted with 3×100 ml of ethyl acetate. The organic extracts are washed with 200 ml of water, dried over magnesium sulfate and subsequently treated with a solution of 341 mg (2.94 mmol) of fumaric acid in 10 ml of methanol. The solution is subsequently concentrated to a volume of 30 ml. After filtration, 800 mg (64%) of the title compound are isolated. M.p.: 143° C. (dec.).

5b. 7-Benzyloxy-1-isobutyl-2-methyl-3-nitropyrrolo[2,3-d]pyridazine 18.3 ml (177 mmol) of benzyl alcohol are added dropwise at room temperature to a solution of 33.0 g (295 mmol) of potassium tert-butoxide and 1.5 g (5.9 mmol) of [18]crown-6 in 180 ml of anhydrous N-methylpyrrolidone. The mixture is subsequently stirred at room temperature for a further 1 h. A solution of 15.9 g (59 mmol) of 7-chloro-1- isobutyl-2-methyl-3-nitropyrrolo[2,3-d]pyridazine in 50 ml of anhydrous N-methylpyrrolidone is then added dropwise in the course of 15 min. The suspension is then stirred at 80° C. for 2 h. After cooling to room temperature, it is treated with 400 ml of ice-water, and extracted with 3×300 ml of ethyl acetate. The organic extracts are washed with 3×200 ml of water and subsequently dried over magnesium sulfate. The residue which remains after concentration is chromatographed on silica gel (eluent: toluene/ethyl acetate=4:1). After concentration of the fractions of Rf=0.25 and crystallization from diisopropyl ether/ethyl acetate, 5.1 g (25%) of the title compound are isolated. M.p.: 162°–164° C.

5c. 7-Chloro-1-isobutyl-2-methyl-3-nitropyrrolo[2,3-d]pyridazine 16.0 g (71.5 mmol) of 7-chloro-1-isobutyl-2-methylpyrrolo[2,3-d]pyridazine are dissolved in portions at 0° C. with vigorous stirring in a mixture of 100 ml of fuming nitric acid and 50 ml of conc. sulfuric acid. The solution is stirred at room temperature for a further 4 h and subsequently introduced into 400 ml of ice-water. The mixture is then neutralized with 10 N sodium hydroxide solution and extracted with 3×250 ml of ethyl acetate. The organic extracts are dried over magnesium sulfate and concentrated. After crystallization from diisopropyl ether/ethyl acetate, 15.9 g (82%) of the title compound are isolated. M.p.: 96° C. (dec.).

6. 1-Benzyl-7-benzylamino-3-bromo-2-methylpyrrolo[2,3-d]pyridazine

A solution of 1.0 g (2.97 retool) of 1-benzyl-3 -bromo-7-chloro-2-methylpyrrolo [2,3-d]pyridazine in 5 ml of benzylamine is heated to 150° C. for 5 h and subsequently cooled to room temperature. The solution is then treated with 50 ml of water, adjusted to pH 6 with 2 N hydrochloric acid and extracted with 2×50 ml of dichloromethane. The organic extracts are dried over magnesium sulfate and concentrated. The residue which remains is chromatographed on silica gel (eluent: toluene/dioxane=2:1). After concentration of the fractions of Rf=0.25 and crystallization from diisopropyl ether, 1.01 g (84%) of the title compound are isolated. M.p.: 185°–188° C.

7a. 3-Acetoxymethyl-1-benzyl-7-benzyloxy-2-methylpyrrolo[2,3-d]pyridazine

A solution of 1.65 g (4.59 mmol) of 1-benzyl-7-benzyloxy-3-hydroxymethyl-2-methylpyrrolo [2,3-d]pyridazine, 3.8 g (18.6 mmol) of dicyclohexylcarbodiimide and 1.6 ml (27.4 mmol) of glacial acetic acid in 50 ml of anhydrous tetrahydrofuran is stirred at room temperature for 18 h. The solution is then treated with 50 ml of water, rendered neutral with saturated sodiumhydrogen carbonate solution and extracted with 3×50 ml of dichloromethane. The organic extracts are washed with 50 ml of water, dried over magnesium sulfate and concentrated. The residue which remains is chromatographed on silica gel (eluent: ethyl acetate). After crystallization from diisopropyl ether, 1.3 g (71%) of the title compound are isolated. M.p.: 121°–122° C.

7b. 3-Acetoxymethyl-1-benzyl-7-(4-fluorobenzyloxy)-2-methylpyrrolo[2,3-d]pyridazine 0.1 g (0.26 mmol) of 1-benzyl-7-(4-fluorobenzyloxy)-3-hydroxymethyl-2-methylpyrrolo [2,3-d]pyridazine, 0.164 g (0.8 mmol) of dicyclohexylcarbodiimide and 0.046 ml (0.8 mmol) of glacial acetic acid are reacted in 5 ml of anhydrous tetrahydrofuran as described for Example 7a. Yield: 55%, m.p.: 109°–110° C.

7c. 1-Benzyl-7-(4-fluorobenzyloxy)-3-methoxyacetoxymethyl-2-methylpyrrolo [2,3-d]pyridazine 0.1 g (0.25 mmol) of 1-benzyl-7-(4-fluorobenzyloxy)-3-hydroxymethyl-2-methylpyrrolo [2,3-d]pyridazine, 0.164 g (0.8 mmol) of dicyclohexylcarbodiimide and 0.061 ml (0.8 mmol) of methoxyacetic acid are reacted in 5 ml of anhydrous tetrahydrofuran as described for Example 7a. Yield: 60%, m.p.: 119°–121° C.

8. Mono-(1-benzyl-7-benzyloxy-2-methylpyrrolo[2,3-d]pyridazine-3-yl) methyl succinate A solution of 0.2 g (0.55 mmol) of 1-benzyl-7-benzyloxy-3-hydroxymethyl-2-methylpyrrolo [2,3-d]pyridazine and 72 mg (0.72 mmol) of succinic anhydride in 10 ml of anhydrous tetrahydrofuran is heated to reflux for 5 h. After cooling to room temperature, the precipitate is filtered off with suction, washed with ethyl acetate and dried in a high vacuum. 0.12 g (48%) of the title compound is isolated. M.p.: 189°–190° C.

Starting compounds

Aa. 1-Benzyl-7-chloro-2-methylpyrrolo[2,3-d]pyridazine

A suspension of 2.0 g (8.3 mmol) of 1-benzyl-2-methyl-6,7-dihydropyrrolo[2,3-d]pyridazine 7-one in 20 ml of phosphorus oxychloride is stirred at 85° C. for 7 h. The excess phosphorus oxychloride is subsequently distilled off and the residue is hydrolyzed in 50 ml of water. After neutralization with 2 N sodium hydroxide solution, the mixture is extracted with 3×50 ml of dichloromethane. The organic extracts are washed with 50 ml of water, dried over magnesium sulfate and concentrated. The residue is recrystallized from methanol. 1.8 g (84%) of the title compound are isolated. M.p.: 152°–156° C.

The following are prepared in an analogous manner:

Ab. 7-Chloro-1-(4-methoxybenzyl)-2-methylpyrrolo[2,3-d]pyridazine 17.8 g (66 mmol) of 1-(4-methoxybenzyl)-2-methyl-6,7-dihydropyrrolo[2,3-d]pyridazine-7-one are reacted at 100° C. for 2 h in 130 ml of phosphorus oxychloride. Purification: chromatography on silica gel (eluent: ethyl acetate). Yield: 76%. M.p.: 126°–128° C.

Ac. 7-Chloro-1-isobutyl-2-methylpyrrolo[2,3-d]pyridazine 3.8 g (12 mmol) of 1-isobutyl-2-methyl-6,7-dihydropyrrolo[2,3-d]pyridazine are reacted at 100° C. for 2 h in 30 ml of phosphorus oxychloride. Purification: chromatography on silica gel (eluent: toluene/dioxane=2:1). Yield: 75%. M.p.: 96°–99° C.

Ba. 1-Benzyl-2-methyl-6,7-dihydropyrrolo[2,3-d]pyridazine-7one

A solution of 8.0 g (22 mmol) of 1-benzyl-7-benzyloxy-4-chloro-2-methylpyrrolo[2,3-d] pyridazine (contaminated with about 5% of the isomeric 4-benzyloxy compound) and 5 ml of triethylamine in 800 ml of methanol is hydrogenated with hydrogen for 3 h on 0.8 g of palladium (5%)/carbon catalyst. The catalyst is subsequently filtered off and the filtrate concentrated to 100 ml. After addition of 20 ml of ethyl acetate and vigorous stirring, the product is filtered off and dried. 3.4 g (65%) of the title compound are isolated. M.p.: 228°–230° C. The isomeric pyridazine-4-one remains in the mother liquor.

The following are prepared in an analogous manner:

Bb. 1-(4-Methoxybenzyl)-2-methyl-6,7-dihydropyrrolo[2,3-d]pyridazine-7-one 38.3 g (97 mmol) of 7-benzyloxy-4-chloro-1-(4-methoxybenzyl)-2-methylpyrrolo[2,3-d] pyridazine (contaminated with about 5% of the isomeric 4-benzyloxy compound), 15 ml of triethylamine and 3.0 g of palladium (5%)/carbon catalyst are hydrogenated with hydrogen for 10 h in 3 l of methanol. Purification: crystallization from methanol. Yield: 69%, m.p.: 212°–213° C.

Bc. 1-Isobutyl-2-methyl-6,7-dihydropyrrolo[2,3-d]pyridazine-7-one 4.5 g (13.6 mmol) of 7-benzyloxy-4-chloro-1-isobutyl-2-methylpyrrolo[2,3-d]pyridazine (contaminated with about 40% of the isomeric 4-benzyloxy compound), 4 ml of triethylamine and 0.5 g of palladium (5%)/carbon catalyst are hydrogenated with hydrogen for 5 h in 500 ml of methanol. Purification: chromatography on silica gel (eluent: toluene/dioxane 4:1). Yield: 52%, m.p.: 188°–191° C.

Ca. 1-Benzyl-7-benzyloxy-4-chloro-2-methylpyrrolo[2,3-d]pyridazine and 1-benzyl-4-benzyloxy-7-chloro-2-methylpyrrolo[2,3-d]pyridazine A solution of 4.3 g (39.8 mmol) of benzyl alcohol in 10 ml of anhydrous tetrahydrofuran is added dropwise in the course of 10 min to a suspension of 1.2 g of 80% strength sodium hydride (42 mmol) in 25 ml of anhydrous tetrahydrofuran. The mixture is stirred for a further 1 h and subsequently slowly added dropwise at 20° C. to a solution of 11.2 g (38.3 mmol) of 1-benzyl-4,7-dichloro-2-methylpyrrolo[2,3-d]pyridazine in 50 ml of anhydrous tetrahydrofuran. The solution is stirred at 20° C. for a further 30 min, subsequently treated with 150 ml of water and extracted with 3×100 ml of ethyl acetate. The organic extracts are washed with 150 ml of water, dried over magnesium sulfate and concentrated. Yield: 81%. The isomers are not separated; the mixture is employed directly for the next synthesis stage (see Example Ba.).

The following are prepared in an analogous manner:

Cb. 7-Benzyloxy-4-chloro-1-(4-methoxybenzyl)-2-methylpyrrolo[2,3-d]pyridazine and 4-benzyloxy-7-chloro-1-(4-methoxybenzyl)-2-methylpyrrolo[2,3-d]pyridazine 4.28 g (149 retool) of sodium hydride (80% strength), 16.0 g (149 retool) of benzyl alcohol and 30.0 g (93 retool) of 4,7-dichloro-1-(4-methoxybenzyl)-2-methylpyrrolo[2,3-d]pyridazine are reacted in a total of 150 ml of anhydrous tetrahydrofuran. The isomers are not separated; the mixture is employed directly for the next synthesis stage (see Example Bb.).

Cc. 7-Benzyloxy-4-chloro-1-isobutyl-2-methylpyrrolo[2,3-d]pyridazine and 4-benzyloxy-7-chloro-1-isobutyl-2-methylpyrrolo[2,3-d]pyridazine 1.2 g (40 retool) of sodium hydride (80% strength), 4.4 g (40 mmol) of benzyl alcohol and 7.0 g (27 mmol) of 4,7-dichloro-1-isobutyl-2-methylpyrrolo[2,3-d]pyridazine are reacted in a total of 80 ml of anhydrous tetrahydrofuran. The isomers are not separated; the mixture is employed directly for the next synthesis stage (see Example Bc.).

Da. 1-Benzyl-4,7-dichloro-2-methylpyrrolo[2,3-d]pyridazine

A suspension of 6.2 g (24 mmol) of 1-benzyl-2-methyl-4,5,6,7-tetrahydropyrrolo[2,3-d ]pyridazine-4,7-dione in 30 ml of phosphorus oxychloride is heated to reflux for 2 h. The excess phosphorus oxychloride is subsequently distilled off and the residue is taken up in 100 ml of water. After neutralization with 10 N sodium hydroxide solution, the mixture is extracted with 3×100 ml of ethyl acetate. The organic extracts are washed with 150 ml of water, dried over magnesium sulfate and concentrated. The residue is taken up in 300 ml of toluene/dioxane (9:1) and clarified with silica gel. After concentration, 5.69 g (80%) of the title compound are obtained. M.p.: 122°–124° C.

The following are prepared in an analogous manner:

Db. 4,7-Dichloro-1-(4-methoxybenzyl)-2-methylpyrrolo-[2,3-d]pyridazine 33.0 g (120 mmol) of 1-(4-methoxybenzyl)-2-methyl-4,5-6,7-tetrahydropyrrolo [2,3-d]pyridazine-4,7dione are heated to reflux for 2 h in 175 ml of phosphorus oxychloride. Purification: crystallization from ethyl acetate/diisopropyl ether. Yield: 80%, m.p. 120°–123° C.

Dc. 4,7-Dichloro-1-isobutyl-2-methylpyrrolo[2,3-d]pyridazine 7.0 g (31.6 mmol) of 1-isobutyl-2-methyl-4,5,6,7-tetrahydropyrrolo[2,3-d ]pyridazine-4,7-dione are heated to reflux for 2 h in 50 ml of phosphorus oxychloride. Purification: chromatography on silica gel (eluent: toluene/dioxane = 9:1). Yield: 88%, m.p.: 89° C. (dec.).

Ea. 1-Benzyl-2-methyl-4,5,6,7-tetrahydropyrrolo[2,3-d]pyridazine-4,7-dione

A solution of 175.3 g (0.56 mol) of diethyl 1-benzyl-5-methylpyrrole-2,3-dicarboxylate and 540 ml (11.1 mol) of hydrazine hydrate in 880 ml of diglyme is heated to 110° C. After 2 h, a further 270 ml (5.5 mol) of hydrazine hydrate are added dropwise in the course of 90 min. The mixture is subsequently stirred at 110° C. for a further 16 h. After cooling and addition of 2 l of ice-water, the mixture is adjusted to pH 5 with conc. hydrochloric acid. The precipitate is filtered with suction and washed with 5 l of water. After drying over potassium hydroxide in a high vacuum and precipitating from diisopropyl ether/ethyl acetate, 127.3 g (89%) of the title compound are isolated. M.p.: 322°–324° C.

The following are prepared in an analogous manner:

Eb. 1-(4-Methoxybenzyl)-2-methyl-4,5,6,7-tetrahydropyrrolo[2,3-d ]pyridazine-4,7-dione 46.0 g (0.133 mol) of diethyl 1-(4-methoxybenzyl)-5-methylpyrrole-2,3-dicarboxylate and 129.5 ml (2.66 mol) of hydrazine hydrate are reacted at 110° C. for 18 h in 290 ml of diglyme. Purification: precipitation from diisopropyl ether/ethyl acetate. Yield: 87%, m.p.: 300° C.

Ec. 1-Isobutyl-2-methyl-4,5,6,7-tetrahydropyrrolo[2,3-d]pyridazine-4,7-dione 9.0 g (31.9 mmol) of diethyl 1-isobutyl-5-methylpyrrolo-2,3-dicarboxylate and 48 ml (985 mmol) of hydrazine hydrate are reacted at 110° C. for 18 h in 50 ml of diglyme. Purification: precipitation from diisopropyl ether/ethyl acetate. Yield: 62%, m.p.: 278°–282° C.

Commercial applicability

The compounds of the formula I and their salts have useful pharmacological properties which make them commercially utilizable. In particular, they exhibit a marked inhibition of gastric acid secretion and an excellent gastrointestinal protective effect in warm-blooded animals. Moreover, the compounds according to the invention are distinguished by a high selectivity of action, the absence of significant side effects and a large therapeutic breadth.

"Gastrointestinal protection" in this connection is understood as meaning the prevention and treatment of gastrointestinal diseases, in particular gastrointestinal inflammatory diseases and lesions (such as e.g. gastric ulcer, duodenal ulcer, gastritis, hyperacidic or medicament-related functional gastropathy which can be caused, for example, by microorganisms (e.g. Helicobacter pylori), bacterial toxins, medicaments (e.g. certain anti-inflammatories and antirheumatics), chemicals (e.g. ethanol), gastric acid or stress situations.

In their excellent properties, the compounds according to the invention surprisingly prove clearly superior to the compounds known from the prior art in various models in which the antiulcerogenic and the antisecretory properties are determined. As a result of these properties, the compounds of the formula I and their pharmacologically tolerable salts are outstandingly suitable for use in human and veterinary medicine, where they are used in particular for the treatment and/or prophylaxis of disorders of the stomach and/or intestine.

The invention therefore further relates to the compounds according to the invention for use in the treatment and/or prophylaxis of the abovementioned diseases.

Likewise, the invention comprises the use of the compounds according to the invention for the production of medicaments which are employed for the treatment and/or prophylaxis of the abovementioned diseases.

The invention furthermore comprises the use of the compounds according to the invention for the treatment and/or prophylaxis of the abovementioned diseases.

The invention further relates to medicaments which contain one or more compounds of the formula I and/or their pharmacologically tolerable salts.

The medicaments are prepared by processes which are known per se and familiar to the person skilled in the art. The pharmacologically active compounds according to the invention (=active compounds) are employed as medicaments either as such, or preferably in combination with suitable pharmaceutical auxiliaries or excipients in the form of tablets, coated tablets, capsules, suppositories, plasters (e.g. as TTS), emulsions, suspensions or solutions, the active compound content advantageously being between 0.1 and 95%.

The auxiliaries or excipients which are suitable for the desired pharmaceutical formulations are familiar to the person skilled in the art on the basis of his expert knowledge. Antioxidants, dispersants, emulsifiers, antifoams, flavor correctants, preservatives, solubilizers, colorants or in particular permeation promoters and complexing agents (e.g. cyclodextrins), for example, can be used in addition to solvents, gelling agents, suppository bases, tablet auxiliaries and other active compound excipients.

The active compounds can be administered orally, parenterally or percutaneously.

In general, it has proven advantageous in human medicine to administer the active compound or active compounds in the case of oral administration in a daily dose of about 0.01 to about 20, preferably 0.05 to 5, in particular 0.1 to 1.5 mg/kg of body weight, if appropriate in the form of several, preferably 1 to 4 individual doses to achieve the desired result. In the case of parenteral treatment, similar or (in particular in the case of intravenous administration of the active compounds) generally lower doses can be used. Any person skilled in the art can easily fix the optimum dose and type of administration of the active compounds necessary in each case on the basis of his expert knowledge.

If the compounds and/or salts according to the invention are to be employed for the treatment of the above-mentioned diseases, the pharmaceutical preparations can also contain one or more pharmacologically active constituents of other pharmaceutical groups, such as antacids, for example aluminum hydroxide, magnesium aluminate; tranquilizers, such as benzodiazepines, for example diazepam; spasmolytics, such as e.g. bietamiverine, camylofin, anticholinergics, such as e.g. oxyphencyclimine, phencarbamide; local anesthetics, such as e.g. tetracaine, procaine; and if desired also enzymes, vitamins or amino acids.

To be emphasized in this connection is in particular the combination of the compounds according to the invention with pharmaceuticals which inhibit acid secretion, such as, for example, $H_2$-blockers (e.g. cimetidine, ranitidine), or further with so-called peripheral anti-cholinergics (e.g. pirenzepine, telenzepine) and also with gastrin antagonists with the aim of increasing the principal action in an additive or superadditive sense and/or eliminating or reducing the side effects, or further the combination with antibacterial substances (such as e.g. cephalosporins, tetracyclines, nalidixic acid, penicillins or alternatively bismuth salts) for the control of Helicobacter pylori.

Pharmacology

The excellent gastric protective effect and the gastric secretion-inhibiting effect of the compounds according to the invention can be detected in investigations on animal experimental models. The compounds according to the invention investigated in the model given below have been provided with numbers which correspond to the numbers of these compounds in the examples.

Investigation of the secretion-inhibiting effect on the perfused rat stomach

The effect of the compounds according to the invention after intravenous administration on the acid secretion of the perfused rat stomach stimulated by pentagastrin in vivo is shown in the following Table 2.

TABLE 2

| No. | N (Number of animals) | Dose (µmol/kg) i.v. | Maximum inhibition of acid secretion | |
|---|---|---|---|---|
| | | | (%) | approx. ED50 +) (µmol/kg) i.v. |
| 1a | 3 | 0.3 | 22 | 1.1 |
| | 3 | 1.0 | 52 | |

TABLE 2-continued

| No. | N (Number of animals) | Dose (μmol/kg) i.v. | Maximum inhibition of acid secretion (%) | approx. ED50 +) (μmol/kg) i.v. |
|---|---|---|---|---|
| | 3 | 3.0 | 70 | |
| | 3 | 10.0 | 94 | |

+) ED50 = dose (interpolated) which causes a maximum inhibition of HCl secretion by 50%.

Method

The abdomen of anesthesized rats (CD rats, female, 200–250 g; 1.5 g/kg i.m. of urethane) was opened after tracheotomy by a median upper abdominal incision and a PVC catheter was fixed transorally in the esophagus and a further one via the pylorus in such a way that the ends of the tubes just projected into the stomach lumen. The catheter leading from the pylorus led outwards via a side opening in the right-hand abdominal wall.

After thorough irrigation (about 50–100 ml), a flow of warm physiological NaCl solution at 37° C. was continuously passed through the stomach (0.5 ml/min, pH 6.8–6.9; Brun-Unita I). The pH (pH meter 632, glass electrode EA 147; φ=5 mm, Metrohm) was determined in the effluent collected (25 ml measuring cylinder) at 15 min intervals in each case and the secreted HCl by titration with a freshly prepared 0.01 N NaOH solution to pH 7 (Dosimat 655 Metrohm).

The stimulation of gastric secretion was effected by continuous infusion of 1 μg/kg (=1.65 ml/h) i.v. of pentagastrin (left femoral vein) about 30 min after the end of the operation (i.e. after determination of 2 preliminary fractions). The substances to be tested were administered intravenously (left jugular vein) in a 1 ml/kg liquid volume 60 min after the start of continuous pentagastrin infusion.

The body temperature of the animals was kept at a constant 37.8°–38° C. by infrared irradiation and heating pads (automatic, stepless control via rectal temperature sensor).

The maximum decrease in acid secretion (15 min fractions) of each treated group compared to that of the untreated control group (=100%) was used as a measure of the secretion-inhibiting effect. The ED50 indicates that dose which causes a maximum inhibition of HCl secretion by 50%.

I claim:

1. A compound of the formula I

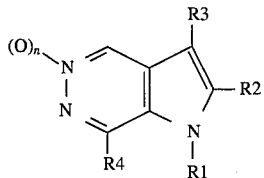

(I)

in which

R1 is 1–4C-alkyl or R5-substituted 1–3C-alkylene,

R2 is 1–4C-alkyl,

R3 is hydrogen, halogen, CHO (formyl), hydroxy-methyl, nitro, amino or the substituent —CH$_2$O—COR7, R4 is halogen or the substituent —A—B—R6, R5 is furyl, thienyl, tetrahydrofuryl, phenyl or phenyl substituted by one or two identical or different substituents from the group consisting of halogen, 1–4C-alkyl and 1–4C-alkoxy, R6 is hydrogen, thienyl, furyl, phenyl or phenyl substituted by one or two identical or different substituents from the group consisting of halogen, 1–4C-alkyl, 1–4C-alkoxy, nitro, —NH—CO—NH$_2$ (ureido), amino, 1–4-C-alkylcarbonylamino and 1–4C-alkoxycarbonylamino, R7 is 1–4C-alkyl, 1–4C-alkoxy-1–4C-alkyl, 1–4C-alkoxycarbonyl-1–4-C-alkyl or carboxy-1–4C-alkyl, A is O (oxygen) or NH, B is a valence bond, —CH$_2$— (methylene) or —CH$_2$CH$_2$— (1,2-ethylene) and n is the number 0 or 1, or a salt thereof.

2. A compound of the formula I as claimed in claim 1, wherein

R1 is 1–4C-alkyl or R5-substituted 1–3C-alkylene,

R2 is 1–4C-alkyl,

R3 is hydroxymethyl, nitro, amino or the substituent —CH$_2$O—COR7,

R4 is the substituent —A—B—R6,

R5 is furyl, thienyl, tetrahydrofuryl, phenyl or phenyl substituted by one or two identical or different substituents from the group consisting of halogen, 1–4C-alkyl and 1–4C-alkoxy, R6 is thienyl, furyl, phenyl or phenyl substituted by one or two identical or different substituents from the group consisting of halogen, 1–4C-alkyl, 1–4C-alkoxy, nitro, —NH—CO—NH$_2$ (ureido), amino, 1–4C-alkylcarbonylamino and 1–4C-alkoxycarbonylamino, R7 is 1–4C-alkyl, 1–4C-alkoxy-1–4C-alkyl, 1–4C-alkoxycarbonyl-1–4C-alkyl or carboxy-1–4C alkyl, A is O (oxygen) or NH, B is —CH$_2$— (methylene) or —CH$_2$CH$_2$— (1,2-ethylene) and n is the number 0 or 1, or a salt thereof.

3. A compound of the formula I as claimed in claim 1, wherein

R1 is isobutyl or R5-substituted methylene,

R2 is 1–4C-alkyl,

R3 is hydroxymethyl, nitro, amino or the substituent —CH$_2$O—COR7,

R4 is the substituent —A—B—R6,

R5 is furyl, thienyl, phenyl or phenyl substituted by one or two identical or different substituents from the group consisting of halogen, 1–4C-alkyl and 1–4C-alkoxy, R6 is thienyl, phenyl or phenyl substituted by one or two identical or different substituents from the group consisting of halogen, 1–4C-alkyl, 1–4C-alkoxy, —NH—CO—NH$_2$ (ureido), amino, 1–4C-alkylcarbonylamino and 1–4C-alkoxycarbonylamino, R7 is 1–4C-alkyl, 1–4C-alkoxy-1–4C-alkyl-1–4C-alkoxycarbonyl-1–4C-alkyl or carboxy-1–4C-alkyl, A is O (oxygen) or NH, B is —CH$_2$— (methylene) and n is the number 0 or 1, or a salt thereof.

4. A compound of the formula I as claimed in claim 1, wherein

R1 is R5-substituted methylene,

R2 is 1–4C-alkyl,

R3 is hydroxymethyl, amino or the substituent —CH$_2$O—COR7,

R4 is the substituent —A—B—R6,

R5 is phenyl or phenyl substituted by a substituent from the group consisting of chlorine, fluorine and 1–4C-alkoxy, R6 is phenyl or phenyl substituted by a substituent from the group consisting of chlorine and fluorine, R7 is methyl, methoxymethyl, methoxycarbonylmethyl, methoxycarbonylethyl, carboxymethyl or carboxyethyl, A is O (oxygen), B is —CH$_2$— (methylene) and n is the number 0, or a salt thereof.

5. 1-Benzyl-7-(4-fluorobenzyloxy)-3-hydroxymethyl-2-methylpyrrolo [2,3-d]pyridazine, or a salt thereof.

6. A compound of claim 1 wherein R3 is halogen.

7. A compound of claim 1 wherein R3 is CHO.

8. A compound of claim 1 wherein R3 is hydroxymethyl.

9. A compound of claim 1 wherein R3 is nitro.

10. A compound of claim 1 wherein R3 is amino.

11. A compound of claim 1 wherein R3 is the substituent —CH$_2$)—COR7.

12. A medicament composition containing a suitable pharmaceutical auxiliary or excipient and an effective amount of one or more compounds as claimed in claim 1 and/or a pharmacologically tolerable salt thereof.

13. A method for preventing or treating a gastrointestinal disease which comprises administering to a patient subject to or afflicted with such disease an effective amount of a compound of claim 1 or a pharmacologically tolerable salt thereof.

* * * * *